United States Patent [19]

Lather et al.

[11] 4,240,281
[45] Dec. 23, 1980

[54] AUTOMATIC SELF-CHECKING OF TEST EQUIPMENT

[75] Inventors: Dieter Lather, Rheurdt; Karl Ries, Mülheim an der Ruhr, both of Fed. Rep. of Germany

[73] Assignee: Mannesmann Aktiengesellschaft, Dusseldorf, Fed. Rep. of Germany

[21] Appl. No.: 963,948

[22] Filed: Nov. 27, 1978

[30] Foreign Application Priority Data

Nov. 28, 1977 [DE] Fed. Rep. of Germany ....... 2753472

[51] Int. Cl.³ .......................................... G01N 29/00
[52] U.S. Cl. ................................................. 73/1 DV
[58] Field of Search ............. 73/1 DV, 597, 598, 599, 73/618, 620, 622, 624, 625, 627, 628, 637, 638, 640, 641, 644; 340/5 C; 367/13

[56] References Cited

U.S. PATENT DOCUMENTS

| 3,791,199 | 2/1974 | Toth et al. ............................ 73/628 |
| 3,975,939 | 8/1976 | McLean ............................... 73/1 DV |
| 4,106,326 | 8/1978 | Lather et al. ....................... 73/1 DV |
| 4,130,018 | 12/1978 | Adams et al. ......................... 73/644 |
| 4,131,027 | 12/1978 | Terschuren et al. .................. 73/638 |
| 4,162,636 | 7/1979 | Lather et al. ......................... 73/638 |

Primary Examiner—Stephen A. Kreitman
Attorney, Agent, or Firm—Smyth, Pavitt, Siegemund, Jones & Martella

[57] ABSTRACT

Equipment for ultrasonic testing structural materials includes transducers and test electronics normally operated in sequential test cycles each cycle including the generation of a test pulse to be sent into the test object and subsequently, upon interaction with the test object, return signals (echos) are received and processed, e.g. as to transit time, amplitude, contour, etc. Self-checking is carried out in three phases. One phase uses simulated receiver signals for operatively disconnected transducers, to be processed by the electronics as if they were echos; a second phase uses simulated transducer inputs and analogous processing and a third phase uses a reference body as test body simulation for conduction of "tests". The results of signal processing are compared with reference signals and correlation of deviations and absence of deviations is used to isolate malfunctions.

15 Claims, 7 Drawing Figures

AUTOMATIC SELF-CHECKING OF TEST EQUIPMENT

BACKGROUND OF THE INVENTION

The present invention relates to a method for automatic self-monitoring or checking the proper functioning of nondestructive test equipment, and more particularly, the invention relates to self-checking of ultrasonic test equipment operated on the basis of sequential test cycles wherein the self-checking may be run as a test cycle or cycles.

Ultrasonic test equipment as they have been used are tested as to their proper functioning to a limited extent only. Usually, the function of the circuitry is indirectly checked during initialization or calibration of the equipment under utilization of dummies, reference standards or the like. The proper function becomes in effect that function carried out under the particular conditions of adjustment of the circuit when cooperating with such a reference or dummy. An example for calibration is, for example, disclosed in U.S. Pat. No. 4,101,326. On the other hand, one tests usually the function of individual components only, and adjusts them in accordance with specifications but without checking the entire system as to all of its complete functioning. Practice has shown that malfunctions of and in complex test installation requires extensive search operations for purposes of fault isolation which procedure can be carried out only by particularly trained personnel and are more often than not rather time-consuming.

The function tests as carried out and usually limited to checking on the transfer function for particular amplitude inputs. Other criteria such as mechanical wear, unintended misalignments of mechanical components, long term aging and drift of electronic components, etc., are usually caught only when the installation is recalibrated and adjusted. "Creeping defects" or the like may well not be caught in that fashion but are "brushed over" simply by retuning, trimming or other adjustment. Mutually compensating defects and even severe defects which do not yet result in complete component failure may well not be recognized in that manner as long as the available adjustment ranges permit compensation.

DESCRIPTION OF THE INVENTION

It is an object of the present invention to provide a method for self-checking of nondestructive test equipment which remedies the deficiencies outlined above and checks on the entire test equipment under utilization of the usual test cycle type of operation of that equipment under generation of definite results permitting immediate isolation of defects, malfunctions, even detection of impending failures or the like.

In accordance with the preferred embodiment of the present invention, it is suggested to provide self-checking on the basis of a three phase check mode. In the first phase the transducers of the equipment are functionally disconnected but the equipment is run in that individual test cycles are performed just as in the case of regular testing except that the receiver channel receives simulated response signals, i.e. electrical signals generated just for this purpose of checking. The equipment is made to respond to and process these signals, whereby in accordance with the test program (being a particular sequence of test cycles involving different channels) the various components participate in the generation of outputs. These outputs must be the same, if this check mode phase is repeated at different times. Each test cycle is preferably repeated several times under utilization of simulated response signals differing in amplitude and/or frequency and/or delay. The second check mode phase involves again a similar or similar type sequence of test cycles, but under inclusion of the transducers; instead of electrically generated simulated receiver signals one uses a simulated echo as transducer input. In the third check mode phase one uses a reference body for well defined interaction with the transducers and the test system, primarily for checking the coupling and positioning features of the system. The three phases together yield directly results which permit isolation of defects in the transducers, the positioning and coupling structure and the test electronics whereby the second and third phases serve also to manifest e.g. for example the correct operation of the transducers and the mechanical coupling devices and structure, so that on the basis of the well defined simulated receiver signals used in the first phase, the output results yield directly meaningful information on any actual or impeding malfunction. The three phases do not have to be run through in the stated sequence.

The invention actually closes the gap in the automatization of ultrasonic testing, and renders the function tests independent from usually empirical experience of maintenance personnel. In fact, the invention introduces true diagnostics into such a system. The check mode can be run at any time and may well be included as part of the overall test program. The check mode may be established automatically from time to time, whereby, however, not all three phases need to be run through.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

Figure 1:
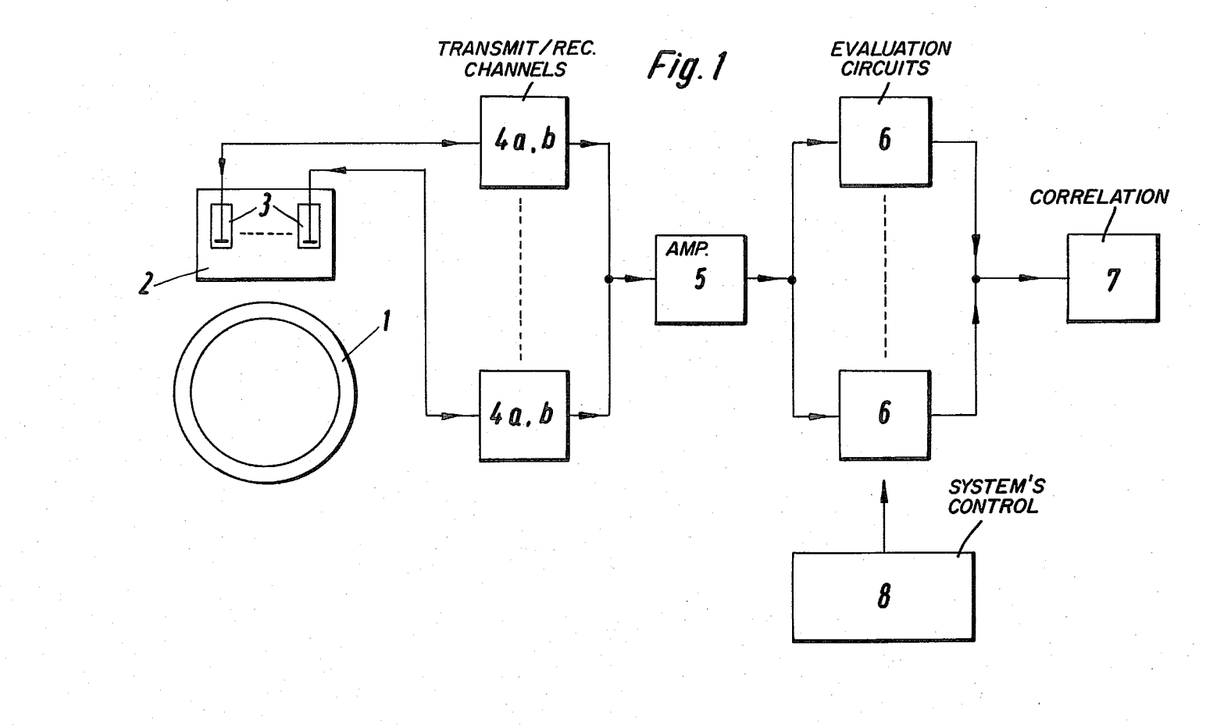
FIG. 1 is a block diagram of an ultrasonic test device, circuit and system of the type to which the invention pertains.

Proceeding now to the detailed description of the drawings, FIG. 1 shows test equipment for testing, for example, tubes or pipes such as 1. The test equipment includes a plurality of transducers 3 which are suitably arranged in relation to the test object 1. The tube 1 is moved during testing in axial direction, i.e. at right angles to the plane of the drawing, and the transducers are coupled in various ways to the surface of the test object, for example, in a manner as described in patent application Ser. No. 767,353, filed Feb. 10, 1977, now U.S. Pat. No. 4,131,027. The mechanical coupling and positioning structure for the transducers as collectively indicated by the block 2 is shown in that application. As to individual transducer mounting, see, for example, Ser. No. 856,223, filed Dec. 1, 1977, now U.S. Pat. No. 4,162,636, German printed application No. P 26 55 364.

The transducers 3 are individually connected to electronic transmitter and receiver circuits or channels 4a, b. At least one pair of such circuits 4a, b is selected for each test cycle, and they are enabled and operated during the test cycle alternatingly in sequential phases. In a first phase of a test cycle, a transmitter circuit 4a provides an electrical signal to the respective transducer for launching an ultrasonic test signal. In a second and subsequent phase of the test cycle, the associated receiver circuit 4b is enabled for immediate processing of any return signals if and as received by the same (or another) transducer. In different cases (through-transmission) the transmitter portion 4a for one transducer may be enabled in a first phase of a test cycle while the receiver portion for a different transducer is enabled during a subsequent second phase of the same test cycle. In this sense, the various transducers and/or transducer pairs, and the associated receiver and transmitter circuits, are operated in sequential test cycles to stepwise run through a test cycle sequence composed of multiple test cycles. The test cycle sequence, in turn, is cyclically repeated as the pipe 1 progresses as each sequence tests only a limited portion of the pipe 1; the test conducted in each cycle involves only a portion, zone or feature of that limited portion covered by a sequence. Moreover, in each position of the pipe the different transducers are coupled to different portions of the pipe. Thus, a particular portion of the pipe is tested by and through different transducers during different cycle sequences so that the test program involves several such test cycle sequences.

In accordance with the test cycle sequences and program, the receiver circuits 4b are sequentially coupled to amplifier circuitry 5 which may include but a single amplifier if its dynamic range suffices. Otherwise, one may well use several amplifiers, one at a time for the receiver phase of any test cycle. The output signal or signals of amplifier 5 are primarily echo pulses of various kinds, and are fed to evaluating circuits 6. One or some of these circuits 6, for example, meter the transit time of echo pulses, each transit time beginning usually at the time of launching of a transmitter pulse by a transducer in the transmit mode. Other circuits may meter whether or not a particular transit time of a partial pulse is exceeded as its "normal" arrival time is predetermined. Particular echos are expected to appear (or not to appear) within certain periods from the launch. The appearance of an echo within a particular looking window may qualify and characterise the echo as being the result of reflection on a particular boundary. Other evaluating circuits 6 may establish amplitude discrimination, or minimum amplitude values. Still other circuits may meter the time of occurrence in terms of a transit time when the signal amplitude exceeds a particular level.

The individual measuring values and results may be correlated in a unit 7. The inputs for the unit 7 as derived from the various circuits 6 are, for example, particular amplitudes; particular transit times; and yes/no indications as to presence or absence of particular amplitude criteria. The unit associates individual test results from different test cycles with specific locations of and in the pipe. The correlation may involve plural cycle sequences for purposes of recognizing and identifying a relatively large flaw or defect. The output of unit 7 may be a registration device simply indicating the presence of a defect or at least of a suspected defect. That output portion of unit 7 may well be coupled with a marking device, which marks the location of the pipe suspected to be defective so that subsequently one may inspect this location by means of high intensity X-rays or the like. However, a sophisticated ultrasonic test system may yield already extensive information on a defect.

Reference numeral 8 refers to the internal control of the system, basically providing timing and enabling signals in accordance with the test program. The circuit 8 runs the system from test cycle to test cycle in a sequence as determined by the program. The circuit 8 provides particularly the enabling signals to establish the transmit phases and receiver phases for each test cycle; other enabling signals (test identification numbers or cycle addresses) are provided to enable the particular transducer or transducers and circuits 4a, b participating in a test cycle. The circuit 8 may also provide the requisite timing, time count and gating signals for the stages 6, including, for example, gating signals covering certain periods or looking windows in which particular response and return signals or echos may or must appear. It should be noted that U.S. Letters Patent Ser. No. 816,149, filed: July 15, 1977, now U.S. Pat. No. 4,173,898, discloses a test system in many details that may be used.

One form of functional supervision of the system is provided by responding to a particular echo such as a rear wall echo particularly in the case of metal plate testing, but even the curved walls of a tube disperse some of the incident radiation so that a rear wall echo is also received by an inclined transducer. Such echos can well serve as signals for purposes of supervision. Signals transmitted from a transducer to a different receiving transducer serve also as a check reference. These signals may have been used in one form or another during calibration and initialization, and should recur at particular levels and in particular instances which should remain invariant during a test sequence if the system operates correctly. In conjunction therewith, subsequently repeated calibration serves inherently as function check in accordance with known procedure. This recalibration may require the use of a reference body in lieu of a test body.

Use of a reference body for calibration is particularly useful; the reference body may be of the same type as a test body, e.g. a short section of a pipe of like wall thickness, diameter and material, and known to be defect free but for a (or several) simulated defects such as bores, grooves, etc.

Figure 2:
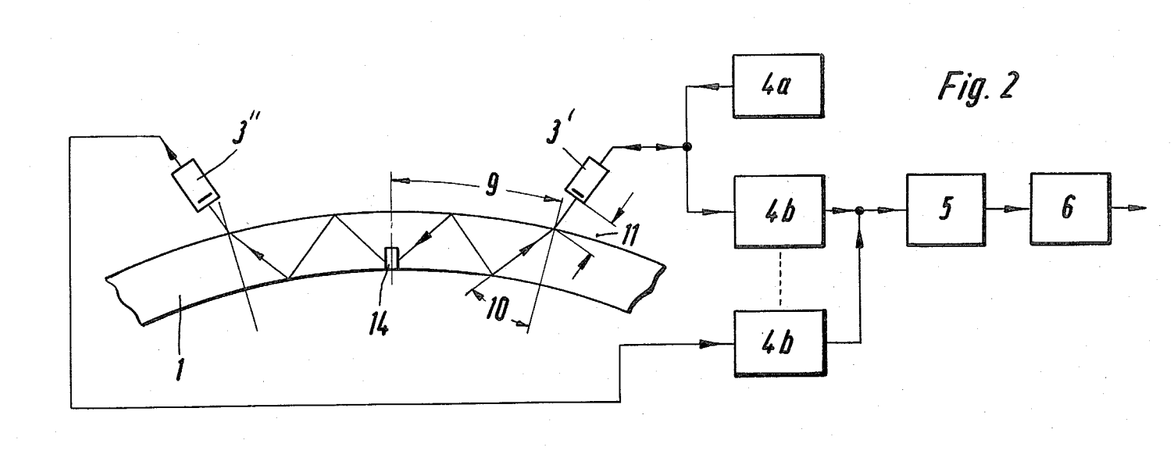
FIG. 2 is a portion of FIG. 1 shown in conjunction with a calibration standard.

Reference numeral 1a in FIG. 2 refers to such a reference body, being a tube with a particular groove 14 as a simulated defect. The figure shows also by way of example two transducers 3' and 3" which are particularly positioned in relation to reference body 1. The position may be exactly the position the transducers will have later in relation to a test body of the same overall geometry.

During calibration, transducer 3' receives an energizing signal from the respective associated transmitter circuit 4a. The energizing signal may already be adjusted here as to duration and steepness of the leading and/or trailing edge; one may use a scope for this purpose. The adjustment may serve to optimize matching of transducer and transmitter.

Of further importance is the distance 11 between the transducer 3' and the point of entrance of the launched ultrasonic pulse. Another parameter is the angle 10 under which the beam actually enters the object. The angle is taken relative to a radial line of the tube 1a.

A signal reflected by the simulated defect 14 will be returned to the transducer 3' in particular angular positions of the tube 1a only. This return echo will be received by the transducer 3' in a subsequent receive phase, and the resulting electrical signal is passed to the particular receiver circuit 4b associated with that transducer for further processing by amplifier 5, including, e.g. rectification. This return echo will be received by a particular evaluating circuit or circuits 6, to be described next.

Figure 3:
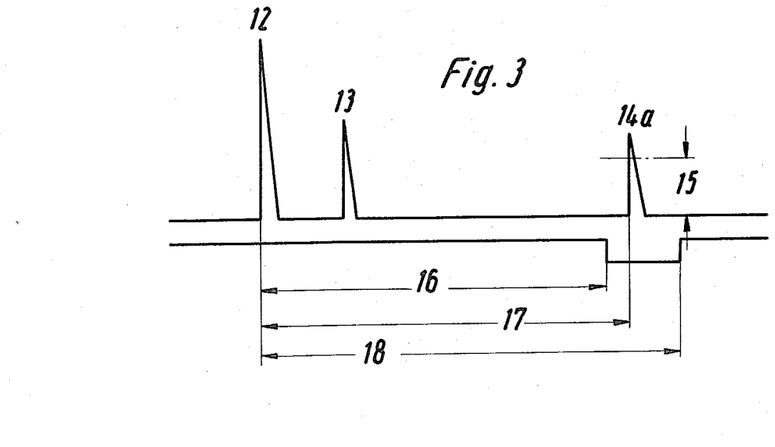
FIG. 3 is a pulse diagram for demonstrating calibration procedure as well as a phase of the self-checking operation.

FIG. 3 is a pulse diagram of the relevant signals as described and others. The first signal 12 is the transmitted signal which is suppressed from the receiver circuits but whose occurrence is otherwise manifested, for example, by causing a time count for circuits 6 to begin to run. The first return signal is an entrance echo 13 resulting from dispersed reflected energy as the launched pulse enters the body 1a. Somewhat later an echo 14a from "flaw" 14 appears. The transit time 17 is a direct indication of the relative location from which the echo was returned. It identifies the zone under inspection in the sense that later, in the field, an echo having a transit time 17 may have originated in a zone having a location corresponding to the location simulated defect 14 had in relation to this particular transducer 3' during calibration. That zone, moreover, is defined by the internal angle 10 of incidence, the distance 11 and the azimuthal distance 9 of that zone from the entrance point of the launched signal.

The zone of expectancy for an echo is actually defined and established by a gating signal whose beginning or leading edge has a transit time equivalent of 16, and which ends at a transit time equivalent 18 in relation to launch time. The resulting looking window brackets, so to speak, a range for return echos which excludes reflections, e.g. from other defects boundaries, etc., along the path of the ultrasonic beam in the object. Please note that on the basis of the materials involved the angle 10 defines the distance 9 for a particular inspection zone. On the other hand, differently phased gating signals brackets different zones from which an echo, if occurring, was returned. The beginning and end of such a gating period can now be adjusted and selected on the basis of this calibration process. The same is true analogously as to amplitudes. The amplitude 14a of the echo from the simulated error is a reference parameter for adjusting, for example, a limit value 15, which, when exceeded during a test run, may trigger an alarm. Other amplitude values can be derived therefrom as alarm limits that must be exceeded. These may involve different evaluating circuits 6.

Criteria for obtaining particular evaluation results and output signals can thus be derived from the calibration run, requiring also individual adjustment of the receiver and transmitter circuits, the gain of any preamplifiers therein, the gain of the main amplifier 5, etc.

The various parameters listed above give also an indication for the required levels and delays of these calibration signals themselves, which in the case of recalibration must be reproduced; if not, one may readjust one or the other of the components which adjustment does not, however, remedy any defects or deterioration in the electronics. Moreover, such an adjustment may not affect at all some components and their operating parameters because they are not or cannot be adjusted.

FIG. 2 illustrates a further supervisory aspect related to the transducer 3", having a symmetrical disposition to transducer 3' with respect to a radial plane (in FIG. 2 "defect" 14 runs through that plane). The transducer 3' may normally be provided for analogous flaw detection, so to speak, from the other side. However, that detector or transducer 3" should also receive a transmitted signal from transducer 3". This kind of supervision, however, results in a signal whose amplitude is the composition of numerous parameters such as geometry and dimensions of the test object (or standard), coupling of both heads to that object, relative disposition, operating parameters of both heads, etc. Thus, the signal as so detected by the second transducer is of significance only as to overall function of a relatively large portion of the test equipment. Moreover, the particular output and receiver circuit 4b used in this case is not the same as the one used by the launching transducer 3' in its subsequent receiver mode. The same may be true for some of the evaluating stages 6.

Figure 4:
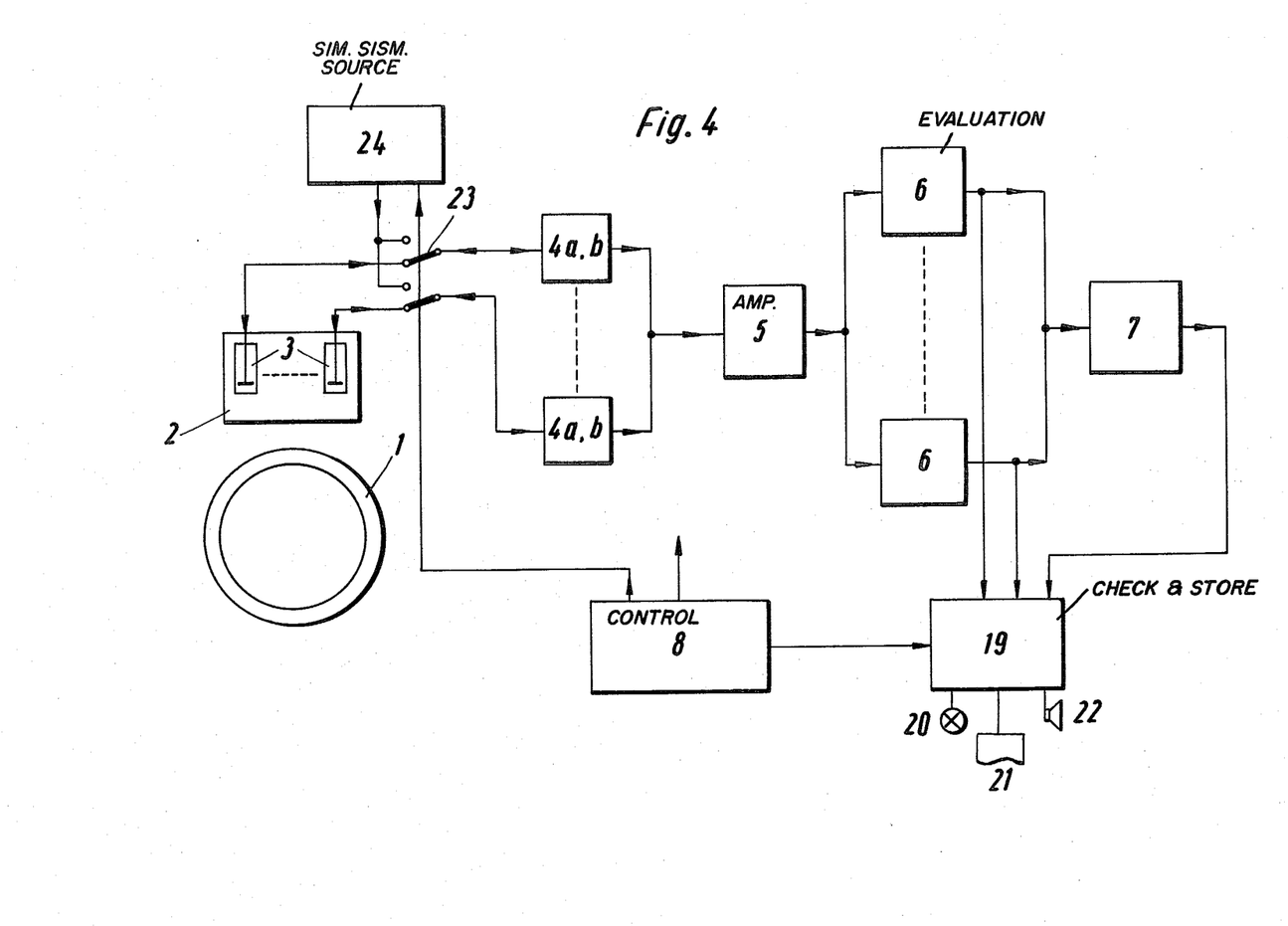
FIG. 4 is a block diagram of the device shown in FIG. 1 but supplemented for self-testing in accordance with the present invention.

FIG. 4 illustrates the ultrasonic test equipment of FIG. 1, but supplemented by the self-checking feature as per the invention. Again, the system includes transducer heads 3, a mechanical mounting structure 2 for the heads, transmitter/receiver circuits 4a, b, the main amplifier 5, evaluating stage 6, processing and output circuit 7, and central control 8.

Deviating from the circuit as described, the transmitter/receiver channels as connected to the individual transducers are subject to switching by switches 23 having normal dispositions for completing the channels as described, while in the alternative positions, the transducers 3 are disconnected from the channels, and a source 24 for pulses and other simulated receiver signals, to be described, is connected to the transmitter/receivers 4a, b instead. The switches 23 are preferably electronic switches, i.e. gates enabled for through connection of the transducer 3 in the regular mode. In the check mode, other gates cause signal transmission to and from circuits 4a, b from and to source 24.

The check mode as defined requires additional circuitry for checking on the outputs of the circuits 6 and/or on the output of the circuit 7. Accordingly, a check unit 19 is provided which receives the signals generated during the check mode and provides comparing functions to check on the correctness of these signals. Unit 19 stores reference data representing proper functioning and the signals generated by circuits 6 in the check mode are compared with these reference data. Unit 19 as well as switch 23 are under control of the timing and control unit 8.

Unit 19 may provide a visible alarm indicator 20, and/or an audible indicator 22, and/or a running recording of the result of the self-checking operation. Important is that the check mode may be established at any time, for example, as a part of the overall test program. The check mode may be run, for example, inbetween two different test objects, i.e. after one pipe has left the stand and the next one has not yet arrived. If the test program as such is quite fast, individual test mode cycles may be interspersed with regular test cycles on a time-sharing or multiprogram-like basis.

Unit 19 will include a storage facility for storing reference data resulting from running, e.g. an initial check mode and test cycle sequence, thereby generating data when the system was found to be correctly operating, for example, following a calibration run. The check mode to be described in detail below yields particular results and these results will be stored as such reference data. Subsequent check modes must yield results that agree with the reference data, if not, alarm is given. However, the device may already include diagnostics in that the check program does not just compare the current results with previous ones, but out of the totality of all results, current ones and previous ones, one may already isolate the defect to a significant extent or at least limit the choice among the components that are defective or deteriorating. The printout 21 may be provided to indicate that kind of ultimate checking.

In order to permit the kind of detailed diagnostics desired, one will need a plurality of different signals to be set by the unit 24 as simulated responses into the system. These different kinds of signals and their uses will be described next.

Self-checking will include, for example, the inspection of circuit sensitivity. It is assumed that the system is in the check mode, and that switches 23 have the alternative position. The control unit 8 now runs the circuit and system through the selected test program as composed of plural, concatenated test cycles. Accordingly, the selected one of the transmitter circuits 4a issues a pulse such as 12 in FIG. 5, which pulse, however, will be set into the unit 24. The control unit 8 will also feed test cycle identification in terms of a test identification number or cycle address to unit 24 to meter a particular period 26, or one of several possible periods to begin with the reception of the transmitter pulse. Following that period, and after the unit 8 has switched from the transmit to the receiver mode, a wave train 25 is issued by the unit 24 and set into the respectively enabled receiver circuit to simulate therein the receiving of a short train of ultrasonic response signals. Frequency and amplitude should be as can be expected under field conditions. That signal now is processed by the circuit 4b, amplifier 5, and by selected ones of the evaluating units 6 which usually participate in the processing of an echo signal from that particular test channel during a particular period. Thus, amplitude comparisons will be made and/or transit times may be measured. The results are all set into unit 19 to be compared with the results obtained in exactly the same manner in previous check mode operations.

The particular transducer operating under a particular cycle address for a particular test cycle may well normally receive different echo signals at different times and during particular different gating periods (looking windows, expectancy ranges). Thus, the same test cycle may be repeated in the check mode, possibly several times. This can be carried out, for example, by and in the control unit 8. This unit as stated includes a cycle address counter (or a software/firm ware type of control) which provides a particular sequence of cycle addresses. In the check mode, rather than running through that sequence in a regular fashion, each (or some) of the addresses are maintained for several test cycles.

Figure 5:
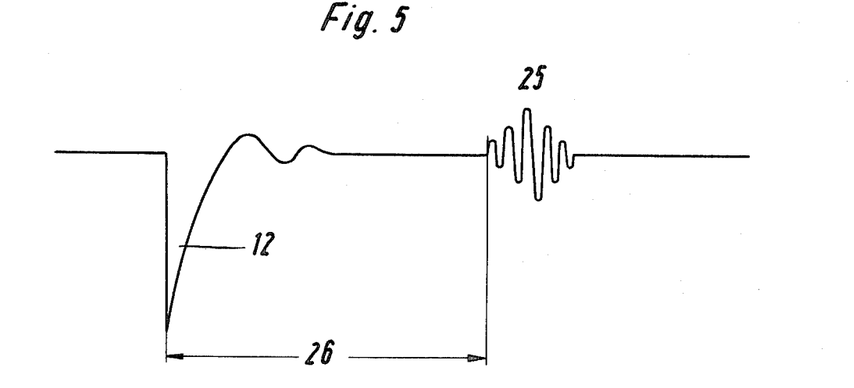
FIG. 5 is an amplitude-time diagram of a launch signal and a simulated receiver signal.

The check test cycles as so repeated, differ specifically in the different times 26 which elapse between the transmit pulse 12 and the generation of a simulated response 25. Conceivably, these response signals may differ in amplitude. In any event, different evaluating stages 6 may be expected to participate or not participate for these different checks and the result in each instance is manifested and was manifested earlier as reference data in unit 19 to be reproduced and repeated by a correctly working system.

By running the entire system through such a sequence of different response signals for a sequence of similar test cycles, and by running the system further through all applicable test cycles in the same fashion, one checks on all components and subsystems of the electronics expected to participate in tests in the field. As stated, differing results and comparisons with references generated in a check mode for that purpose permit diagnostic isolation of defects.

It should be noted that for such comparisons to be reasonably effective, certain tolerances must be permitted. However, the reference storage may permit the detection of a gradual deterioration if, for example, relatively small deviations increase more or less slowly from check mode to check mode; even though the deviation is not yet a malfunction, its gradual increase may be such that it readily indicates impending failure, aging, drift, etc.

Figure 6:
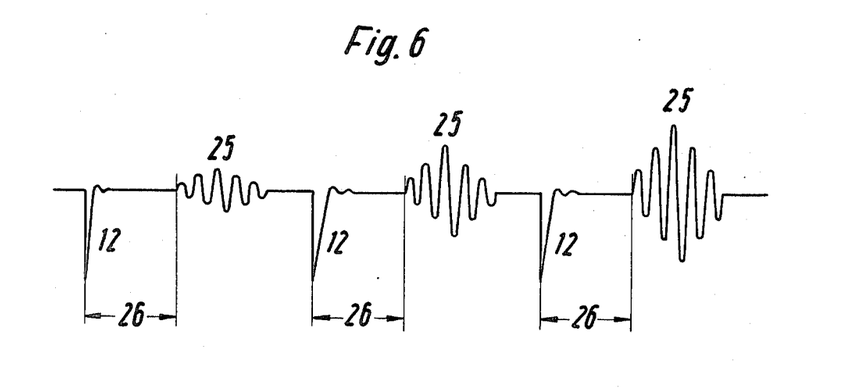
FIG. 6 is a diagram showing a sequence of simulated receiver signals for checking the linearity of components.

A more sophisticated check pattern which combines sensitivity with a check on linearity of and in the test electronics, is shown in FIG. 6. It is again assumed here that the self-check program is not just the regular sequence of test cycles, but the same test cycle, i.e. the test operation by a particular selected transducer is repeated.

Each such test cycle again has a transmit phase in which a trigger pulse 12 is furnished, and in the subsequent receiver phase, unit 24 provides a simulation return signal 25. However, these signals vary in amplitude from cycle to cycle in that in synchronism with the test cycles, the amplitude is, for example, stepwise increased. This can be carried out by stepwise changing the impedance of the output circuit in unit 24 which determines the output level of the respective signal 25.

The signal evaluation is repeated in each test cycle, whereby particularly amplitude evaluation is used to generate different responses. These are again compared in unit 19 with reference data from previous check mode operations to determine the proper functioning and particularly linearity in the responses.

The same type of check can then be conducted under selection of different transducers, i.e. by running through the entire test program with the understanding that each test cycle with the same selected channel is repeated for different amplitudes of simulated return.

Figure 7:
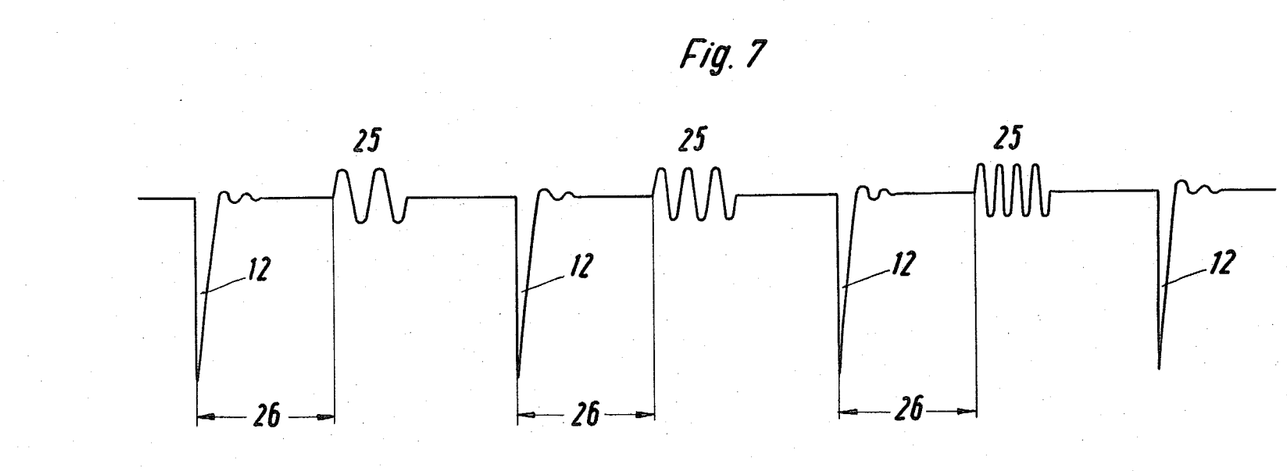
FIG. 7 is a diagram of a sequence of simulated receiver signals to check on the frequency response.

FIG. 7 shows that analogously one can check on the frequency response of and in the test electronic. Again, one runs through the test sequence and program but each test cycle is repeated several times also here, whereby in each such cycle the simulated transducer return has a different frequency. The frequency change can be carried out, e.g. through a VCO or other suitable devices whose output frequency is stepwise changed.

It can readily be seen that a sophisticated self-check program involves for each "normal" test cycle, a plurality of test cycles involving the same transducer or test channel, but the simulated response signals 25 differ in times of occurrence and/or amplitude and/or frequency. This may result in some redundancy, but exactly such redundancy may be valuable for purposes of cross checking.

After having produced data representing the response of the electronics to particular, well defined transducer responses, one phase of the self-checking mode and operation is completed. The check mode now may proceed to the next phase as follows. U.S. Patent application Ser. No. 912,712; filed: June 5, 1978, discloses a transducer in which, in front of the vibrating element, i.e. in a well defined location between the output proper of the transducer and the entry point of the ultrasonic waves into the test object, a small reflector is provided which returns a minute fraction of the launched pulse which, however, is received by the transducer and can be passed on to the receiver circuit. If the transducers 3 are of that type, a check mode phase can now be practiced in which the switch 23 is placed into the illustrated position, but no test object is placed in front of the transducer (for sharing of this check phase, see infra). Again, the test program is run through, but the electronics responds only to this definite return signal by and from the transducers themselves. Only amplitude evaluation circuitry needs to participate in this operation, and the result of the amplitude evaluation is again passed to unit 19. In any event, the amplitude processing circuitry in the electronics will participate in this particular operation, and if the unit 19 detects a deviation in the result from results previously obtained, it will so indicate. Such an "error" indication is per se not indicative of any defect in the transducer as the electronics may be defective. The defect can be localized in the transducer only, if the previously described self-checking of the equipment under utilization of the source 24 did not yield any abnormality.

It will be recalled that in the check mode phase one particular simulated responses (25) were produced by unit 24 at particular delays. One such delay may, for example, be equivalent to the round trip time of a launched pulse when in parts reflected by such a wire across the transducer. Now, in check mode phase two, a true reflection is compared with that reference reflection. If the electronics was found not to be defective in check mode phase one, any deviation of the amplitude of the wire reflection as now detected, can readily be attributed to the transducer. The unit 19 will so indicate.

Since the transducers 3 can be provided with this reflector on a permanent basis, the transducer check can be run at any time. Actually, the reflection produced by the transducer every time it launches an ultrasonic signal, can be used in each normal test cycle right in the beginning of the respective receiver phase to provide a function test. If that test indicates a possible malfunction or deterioration of performance, the system can be switched to the self-check mode for further diagnostics as per phase one. That phase then may establish the defect in the electronics or in the transducer and will so indicate. It can readily be seen that this aspect points to the full automation in the procedure in that the system may automatically go into the self-check mode phase one, and halt the regular testing if a running check during regular testing indicated a possible system defect. The test object remains coupled to the transducers in this case of self-checking, but that coupling is ignored as far as this check mode two or check mode two type operation is concerned. The self-checking uses only the reflection by the wire etc. and not any subsequent echos reaching the transducers. These echos may be processed regularly. This then provides and needs true multiprogramming type of operations in which regular test evaluation and check mode two operations are time-multiplexed, possibly even within the same test cycles.

Alternatively to the utilization of transducers with a built-in reference reflection as per the application Ser. No. 912,712, filed June 5, 1978, one may use a reference element of the type disclosed in patent application Ser. No. 878,240, filed Feb. 16, 1978, now U.S. Pat. No. 4,182,154, (see also German printed application No. P 26 35 982). This element, however, requires the check mode phase two to be run separately.

As far as the complete check mode is concerned, a further phase thereof involving again a complete program sequence, is carried out by causing the equipment to cooperate with test body simulation or a dummy with particular "defects". These defects need not be defined in a manner used for calibration, and initialization, though one may well use the same kind of dummy 1a. The reference date for this third check mode phase may, for example, be generated in the end of an initial calibration, when the system is properly calibrated and presumed to function properly. The test program is run through and the data generated by and in the system will serve as future reference data when the same body 1a is used in check mode phase three.

If the first two self-check phases yield no error, one can assume that the electronics and the transducers operate properly. Now, the same program is run through while this dummy is coupled to the transducers. Again, the result obtained by actually conducting true test sequence should be the same as a result obtained and stored earlier as check mode phase three reference for and in unit 19. In the case of a deviation, the error or malfunction so indicated must be the result of the mechanical interaction such as the mechanical structure 2 coupling the dummy to the transducers, or mechanical structure that positions the test object.

The invention is not limited to the embodiments described above but all changes and modifications thereof not constituting departures from the spirit and scope of the invention are intended to be included.

We claim:

1. Method of self-checking a system for the nondestructive testing of structural materials which includes a plurality of transducers, respectively transmitters and/or receiver channels for the transducers, and signal processing stages connected to the receiver channels, said system operating with a sequence of test cycles wherein at least some of the test cycles use different ones of the transducers, comprising the steps of:

(i) generating simulated receiver signals and setting them into the receiver channels for processing by the processing stages during the said test cycles, for checking the function of the receiver channels and at least some of said stages;

(ii) generating return signals for the transducers for passage by them into the receiver channels but without using any coupling of the transducers to a test object, for processing by the processing stages during a repetition of at least some of said test cycles;

(iii) repeating at least some of said test cycles but using an external reference element for coupling to the transducers and returning thereto signals launched in transmit phases of the particular test cycles as repeated;

storing the result of the processing as per the preceding steps; and using result differences for isolating defects in the system.

2. Method as in claim 1, wherein the step (i) is carried out in a manner repeating each test cycle with different simulated receiver signals.

3. Method as in claim 2 for an ultrasonic test system, wherein said simulated receiver signals differ in at least one of the following aspects, (a) spacing from a simulated launch time; (b) amplitude; (c) frequency.

4. Method as in claim 1, 2 or 3, said reference signals being a group of waves.

5. Method as in claim 1, wherein the external reference element contains simulated defects.

6. Method as in claim 1, including storing the results of an earlier self-checking cycle which includes the steps (i), (ii) and (iii), and comparing therewith the results of later ones of such steps to perform function tests.

7. Method of self-checking a system for the nondestructive testing of structural materials which includes a plurality of transducers, respectively transmitter and/or receiver channels for the transducers, and signal processing stages connected to the receiver channels, said system operating with a sequence of test cycles, wherein at least some of the test cycles use different ones of the transducers, comprising the steps of:

running the system through a sequence of test cycles wherein at least some of the test cycles are repeated several times;

generating different simulated receiver signals each following a simulated launch of a transmitter signal wherein the simulated signals for the repeated test cycles differ in at least one of the following: (i) spacing from the launch; (ii) amplitude; and (iii) frequency;

running the system through another sequence of test cycles under utilization of a reference body into which transmitted signals are launched and from which responses are returned for pick-up by the transducers;

setting in each one of said test cycles the generated receiver signals or the picked-up transducer signals into the receiver channels for processing by the processing stages during the respective test cycles; and comparing the processed signals with reference signals and generating an indication in case of a deviation.

8. Method as in claim 7, wherein the said reference signals as stored resulted from test cycles run through earlier under utilization of said simulated receiver signals.

9. Method as in claim 7 and including the steps of additionally checking the system through a plurality of test cycles by means of signals provided to the transducers from a source external to the transducers.

10. Method as in claim 7, wherein linearity of circuit components is checked by using in sequential repeated test cycles simulated signals of different amplitude under the same spacing and frequency for such signals.

11. Method as in claim 7 wherein the frequency response of circuit components is checked by using in sequential, repeated test cycles simulated signals of different frequencies under the same spacing and amplitude.

12. Method as in claim 7, wherein some of the simulated signals for sequential repeated test cycles have similar amplitude and frequency but different spacing for checking the processing of such signals as to transit time in different looking windows.

13. Method of checking a system for the nondestructive testing of structural materials which includes a plurality of transducers to be coupled to an object to be tested and which further includes electronic circuitry connected to the transducers and operating in parts on a time and/or function sharing basis, the tests being conducted on the basis of plural test cycles involving different transducers comprising the steps of:

(i) generating simulated signals during a sequence of test cycles in which the transducers are operatively disconnected from the circuitry and setting these signals into the circuitry for processing therein in lieu of transducer signals;

(ii) generating simulated input signals for the transducers as connected to the electronic circuitry for and during a sequence of test cycles for processing therein in lieu of signals as returned from a body to the transducers when coupled thereto;

(iii) coupling a reference body to the transducers for return of signals to the transducers as connected to the circuitry for processing therein in different test cycles;

comparing the processed signals as produced during the steps (i), (ii) and (iii) with reference signals; and correlating deviations and absence of deviations of the compared signals from the reference signals to obtain isolation of possible malfunctions of components in the system.

14. Method of self-checking a system for the nondestructive testing of structural materials which includes a plurality of transducers, respectively transmitter and/or receiver channels for the transducers, and signal processing stages connected to the receiver channels, said system operating with a sequence of test cycles, wherein at least some of the test cycles use different ones of the transducers, comprising the steps of:

running the system through a sequence of test cycles wherein at least some of the test cycles are repeated several times;

generating different simulated receiver signals each following a simulated launch of a transmitter signal wherein the simulated signals for the repeated test cycles differ in frequency, under the same spacing and amplitude;

setting the generated receiver signals into the receiver for processing by the processing stages in order to determine the frequency response of circuit components participating in the processing; and comparing the processed signals with reference signals and generating an indication in case of a deviation.

15. Method of self-checking a system for the nondestructive testing of structural materials which includes a plurality of transducers, respectively transmitter and/or receiver channels for the transducers, and signal processing stages connected to the receiver channels, said system operating with a sequence of test cycles, wherein at least some of the test cycles use different ones of the transducers, comprising the steps of:

running the system through a sequence of test cycles wherein at least some of the test cycles are repeated several times;

generating different simulated receiver signals each following a simulated launch of a transmitter signal wherein the simulated signals for the repeated test cycles differ in spacing from the launch, but have similar amplitude and frequency;

setting the generated receiver signals into the receiver channels for processing by the processing stages in different looking windows as generated during the different test cycles; and comparing the processed signals with reference signals and generating an indication in case of a deviation.

* * * * *